US00PP21618P2

(12) United States Plant Patent
Graff

(10) Patent No.: US PP21,618 P2
(45) Date of Patent: Jan. 11, 2011

(54) ***HIBISCUS* PLANT NAMED 'BOREAS'**

(50) Latin Name: *Hibiscus rosa-sinensis*
Varietal Denomination: Boreas

(75) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 0 days.

(21) Appl. No.: 12/589,046

(22) Filed: Oct. 16, 2009

(51) Int. Cl.
*A01H 5/00* (2006.01)

(52) U.S. Cl. ..... Plt./257
(58) Field of Classification Search ..... Plt./257
See application file for complete search history.

*Primary Examiner*—Annette H Para
(74) *Attorney, Agent, or Firm*—C. A. Whealy

(57) ABSTRACT

A new and distinct cultivar of *Hibiscus* plant named 'Boreas', characterized by its upright, somewhat, outwardly spreading and dense and bushy plant habit; glossy dark green-colored leaves; uniform and freely flowering habit; large pale yellow-colored flowers with dark red-colored centers; and good flower longevity.

1 Drawing Sheet

Botanical designation: *Hibiscus rosa-sinensis.*
Cultivar denomination 'Boreas'.

BACKGROUND OF THE INVENTION

The present invention relates to a new and distinct cultivar of *Hibiscus* plant, botanically known as *Hibiscus rosa-sinensis*, and hereinafter referred to by the name 'Boreas'.

The new *Hibiscus* plant is a product of a planned breeding program conducted by the Inventor in Sabro, Denmark. The objective of the breeding program is to create new strong *Hibiscus* plants with attractive and long-lasting flowers.

The new *Hibiscus* plant originated from an open-pollination in August, 2006 in Sabro, Denmark of *Hibiscus rosa-sinensis* 'Caribbean Apricot', not patented, as the female, or seed, parent with an unknown selection of *Hibiscus rosa-sinensis* as the male, or pollen, parent. The new *Hibiscus* plant was discovered and selected by the Inventor as a flowering plant within the progeny of the stated open-pollination in a controlled greenhouse environment in Sabro, Denmark in June, 2007.

Asexual reproduction of the new *Hibiscus* plant by vegetative terminal cuttings in a controlled greenhouse environment in Sabro, Denmark since September, 2007, has shown that the unique features of this new *Hibiscus* plant are stable and reproduced true to type in successive generations.

SUMMARY OF THE INVENTION

Plants of the new *Hibiscus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Boreas'. These characteristics in combination distinguish 'Boreas' as a new and distinct cultivar of *Hibiscus:*

1. Upright, somewhat, outwardly spreading and dense and bushy plant habit.
2. Glossy dark green-colored leaves.

3. Uniform and freely flowering habit.
4. Large pale yellow-colored flowers with dark red-colored centers.
5. Good flower longevity.

Plants of the new *Hibiscus* can be compared to plants of the female parent, 'Caribbean Apricot'. Plants of the new *Hibiscus* differ primarily from plants of 'Caribbean Apricot' in flower longevity as flowers of plants of the new *Hibiscus* last about three to five days whereas flowers of plants of 'Caribbean Apricot' last about one to two days.

Plants of the new *Hibiscus* can be compared to plants of the *Hibiscus rosa-sinensis* 'Cairo White', not patented. In side-by-side comparisons conducted in Sabro, Denmark, plants of the new *Hibiscus* differed from plants of 'Cairo White' in the following characteristics:

1. Plants of the new *Hibiscus* were more freely branching than plants of 'Cairo White'.
2. Plants of the new *Hibiscus* had wider leaves than plants of 'Cairo White'.
3. Plants of the new *Hibiscus* had broader flowers buds than plants of 'Cairo White'.
4. Plants of the new *Hibiscus* had larger flowers than plants of 'Cairo White'.
5. Flowers of plants of the new *Hibiscus* and 'Cairo White' differed slightly in color.
6. Flowers of plants of the new *Hibiscus* lasted about four to five days whereas flowers of plants of 'Cairo White' lasted about one day.

BRIEF DESCRIPTION OF THE PHOTOGRAPH

The accompanying colored photograph illustrates the overall appearance of the new *Hibiscus* plant, showing the colors as true as it is reasonably possible to obtain in colored reproductions of this type. Colors in the photograph may differ slightly from the color values cited in the detailed botanical description which accurately describe the colors of the new *Hibiscus* plant. The photograph comprises a side perspective view of typical flowering plants of 'Boreas' grown in a container.

DETAILED BOTANICAL DESCRIPTION

The aforementioned photograph and following observations, measurements and values describe plants grown in Sabro, Denmark in 12-cm containers in a glass-covered greenhouses during the summer under conditions which closely approximate commercial *Hibiscus* production. During the production of the plants, day temperatures ranged from 20° C. to 25° C., night temperatures ranged from 19° C. to 21° C. and light levels ranged from 40 to 50 klux. Plants were 22 weeks old when the photograph and the description were taken. In the description, color references are made to The Royal Horticultural Society Colour Chart, 2001 Edition, except where general terms of ordinary dictionary significance are used.

Botanical classification: *Hibiscus rosa-sinensis* 'Boreas'.

Parentage:

*Female, or seed, parent.*—*Hibiscus rosa-sinensis* 'Caribbean Apricot', not patented.

*Male or pollen parent.*—Unknown selection of *Hibiscus rosa-sinensis*, not patented.

Propagation:

*Type.*—By vegetative terminal cuttings.

*Time to initiate roots, summer.*—About three weeks at temperatures of 24° C.

*Time to initiate roots, winter.*—About four weeks at temperatures of 24° C.

*Time to produce a rooted young plant, summer.*—About eight weeks at temperatures of 24° C.

*Time to produce a rooted young plant, winter.*—About ten weeks at temperatures of 24° C.

*Root description.*—Medium in thickness, fleshy; color, close to 158A.

*Rooting habit.*—Freely branching; dense.

Plant description:

*Plant and growth habit.*—Upright, somewhat outwardly spreading and dense and bushy plant habit; moderately vigorous growth habit.

*Branching habit.*—Freely branching, usually about five to eight lateral branches develop; pinching enhances lateral branch development.

*Plant height.*—About 35 cm to 55 cm.

*Plant diameter* (*area of spread*).—About 35 cm to 55 cm.

Lateral branch description:

*Length.*—About 18 cm to 30 cm.

*Diameter.*—About 4 mm to 8 mm.

*Internode length.*—About 1 cm to 5 cm.

*Strength.*—Strong.

*Texture.*—Woody.

*Color.*—Close to N198A.

Foliage description:

*Arrangement.*—Alternate, single; numerous; symmetrical.

*Length.*—About 6 cm to 9 cm.

*Width.*—About 6 cm to 10 cm.

*Shape.*—Cordate.

*Apex.*—Acute.

*Base.*—Obtuse, cordate.

*Margin.*—Crenate.

*Texture, upper and lower surfaces.*—Smooth, glabrous.

*Luster, upper surface.*—Glossy.

*Luster, lower surface.*—Matte.

*Venation pattern.*—Pinnate; arcuate.

*Color.*—Developing leaves, upper surface: Close to 135A. Developing leaves, lower surface: Close to 137C. Fully expanded leaves, upper surface: Close to 139A; venation, close to 138A. Fully expanded leaves, lower surface: Close to 137A; venation, close to 138B.

*Petiole.*—Length: About 2 cm to 5 cm. Diameter: About 2 mm. Texture, upper and lower surfaces: Smooth, glabrous. Color, upper surface: Close to 138A. Color, lower surface: Close to 138B.

Flower description:

*Flower arrangement.*—Flowers arranged singly at terminal leaf axils. Uniform, continuous and freely flowering habit with numerous flower buds and/or open flowers per plant at one time; flowers face mostly upright to slightly outwardly.

*Flower appearance.*—Rounded, pale yellow-colored flowers with red-colored centers.

*Fragrance.*—None detected.

*Flower longevity.*—Good flower longevity, flowers last for about four to five days; flowers persistent.

*Natural flowering season.*—Usually spring and summer or during periods of warm weather; plants flower year-round in the greenhouse.

*Flower diameter.*—About 16 cm to 20 cm.

*Flower length* (*height*).—About 11 cm.

*Flower bud.*—Rate of opening: Flowers buds open in about three days. Length: About 7 cm to 9 cm. Diameter: About 2 cm to 3 cm. Shape: Ovate to lanceolate. Color: Close to 154C.

*Petals.*—Arrangement: Corolla consists of five petals that are fused at base; petals imbricate. Length: About 10 cm to 11 cm. Width: About 9 cm to 10 cm. Shape: Obovate. Apex: Rounded. Base: Attenuate. Margin: Entire, undulate. Texture: Glabrous; rugose. Color: When opening, upper surface: Close to 2D; towards the base, close to 53A. When opening, lower surface: Close to 2D. Fully opened, upper surface: Close to 4D; towards the base, close to 53A. Fully opened, lower surface: Close to 2D.

*Sepals.*—Appearance: Five sepals fused into a tubular star-shaped calyx. Length: About 3.5 cm. Width: About 1.2 cm. Shape: Lanceolate. Apex: Acuminate. Margin: Entire. Texture, upper surface: Rough. Texture, lower surface: Smooth. Color, upper surface: Close to 144A. Color, lower surface: Close to 145A.

*Peduncles.*—Length: About 3 cm to 4 cm. Diameter: About 3 mm. Angle: About 20° to 30° from the lateral branch axis. Strength: Strong. Texture: Smooth, glabrous. Color: Close to 144A.

*Reproductive organs.*—Androecium: Stamen number: Numerous, about 100. Filament length: About 4 mm to 5 mm. Filament color: Close to 155D. Anther shape: Rounded to ovate. Anther length: About 1 mm to 2 mm. Anther color: Close to 21D. Amount of pollen: Abundant. Pollen color: Close to 21A. Gynoecium: Pistil length: About 10 cm. Style length: About 9 cm. Style texture: Smooth, waxy. Style color: Close to 46A. Stigma appearance: Five-parted, rounded. Stigma color: Close to 12B. Ovary color: Close to 145A.

*Seeds.*—Quantity produced per flower: About one to twelve. Length: About 4 mm. Diameter: About 4 mm. Color: Close to 202A.

Temperature tolerance: Plants of the new *Hibiscus* have been observed to have tolerate temperatures from about 5° C. to about 30° C.

Pathogen/pest resistance: Plants of the new *Hibiscus* have not been observed to be resistant to pathogens and pests common to *Hibiscus*.

It is claimed:

1. A new and distinct *Hibiscus* plant named 'Boreas' as illustrated and described.

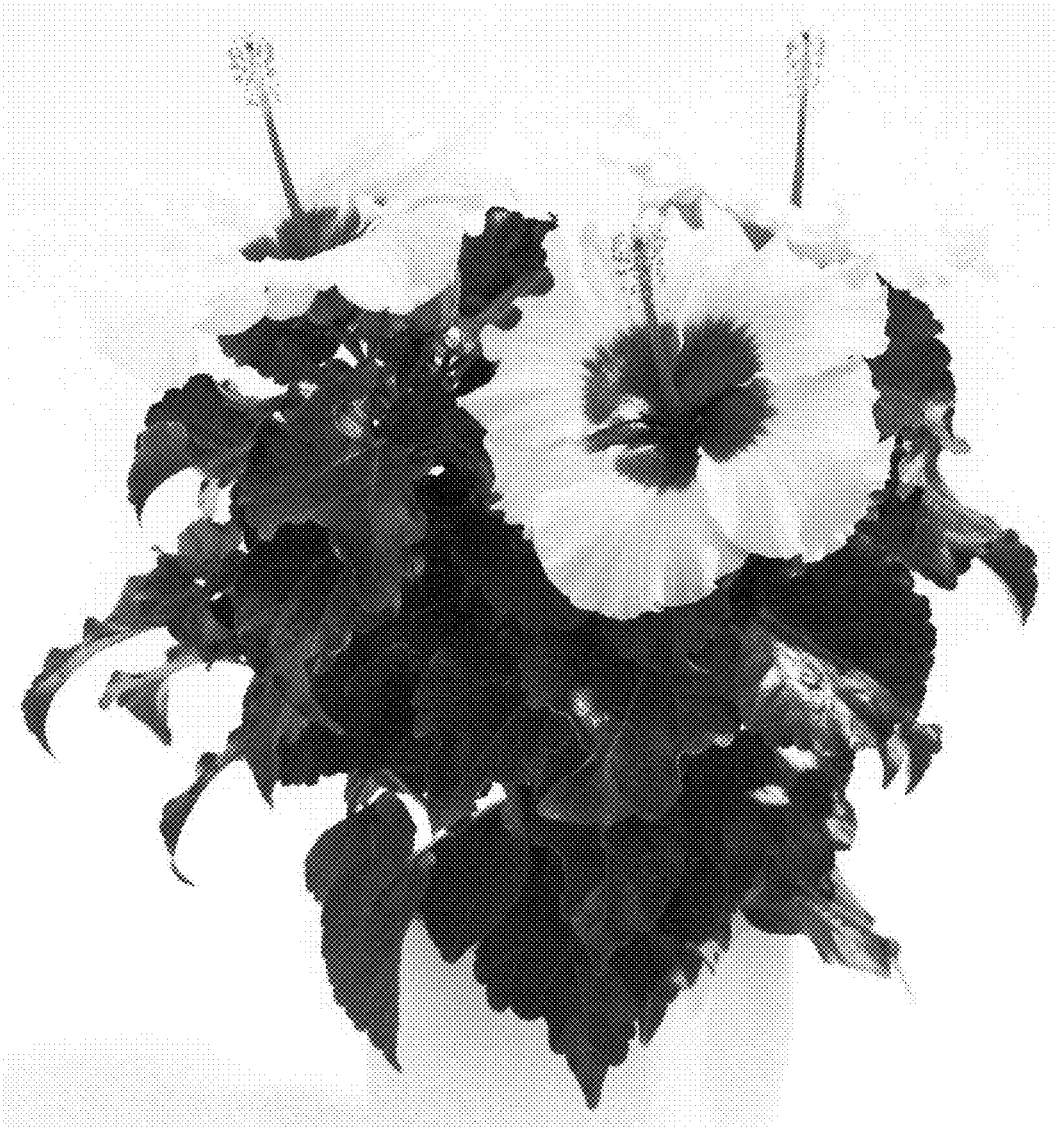

* * * * *